United States Patent [19]
Lange

[11] Patent Number: 5,584,382
[45] Date of Patent: Dec. 17, 1996

[54] APPARATUS FOR DETECTING A CHANGE IN POSITION OF FIRST AND SECOND MEMBERS FOR USE IN MOUNTING THE DETECTOR ARRAY OF A CT SCANNER TO A RADIATION THEAPY SIMULATOR

[76] Inventor: Jon T. Lange, 25111 Arrow Ridge, San Antonio, Tex. 78258

[21] Appl. No.: 486,627

[22] Filed: Jun. 7, 1995

Related U.S. Application Data

[60] Continuation of Ser. No. 194,848, Feb. 14, 1994, abandoned, which is a division of Ser. No. 7,493, Jan. 22, 1993, Pat. No. 5,317,617.

[51] Int. Cl.$^6$ ............................................. H01H 35/00
[52] U.S. Cl. ............................................. 200/330
[58] Field of Search ............................. 200/330, 47

[56] References Cited

U.S. PATENT DOCUMENTS

| | | | |
|---|---|---|---|
| 2,740,023 | 3/1956 | Kryder | 200/330 X |
| 3,196,877 | 7/1965 | Corbin | 200/330 X |
| 4,019,003 | 4/1977 | Duerksen, Jr. | 200/330 X |
| 4,243,857 | 1/1981 | Reis | 200/330 X |

OTHER PUBLICATIONS

Drawing of collision detection device of x–ray simulator marketed by Cascade X–Ray (Yakima, WA), (date of first use of device unknown but known to be prior art).

Cascade X–ray, Radiation Therapy Simulator (date unknown but known to prior art).

Drawing of collision detection device of x–ray simulator marketed by Oldelft USA (Fairfax, VA) (date of first of device unknown but known to be prior art).

Oldelft, Simulix–MC (date unknown but known to be prior art).

*Primary Examiner*—Renee S. Luebke
*Attorney, Agent, or Firm*—Mark R. Wisner

[57] ABSTRACT

Method and apparatus for storing and moving an x-ray detector assembly in and out of the field of radiation produced by a radiation therapy simulator source while remaining affixed to the gantry of the simulator and retaining the functional attributes of a standard radiation therapy simulator cassette holder. When mounted to the simulator, the apparatus of the present invention has the ability to position an x-ray cassette in a fixed position relative to the radiation source, allow for the use of an image intensifier tube by being effectively radiolucent over the tube, and incorporating a mechanism which is capable of absorbing a degree of movement independent of the gantry while simultaneously activating a switch mechanism which can be used to stop gantry rotation, thereby preventing damage to the device or that which it contacts.

4 Claims, 5 Drawing Sheets

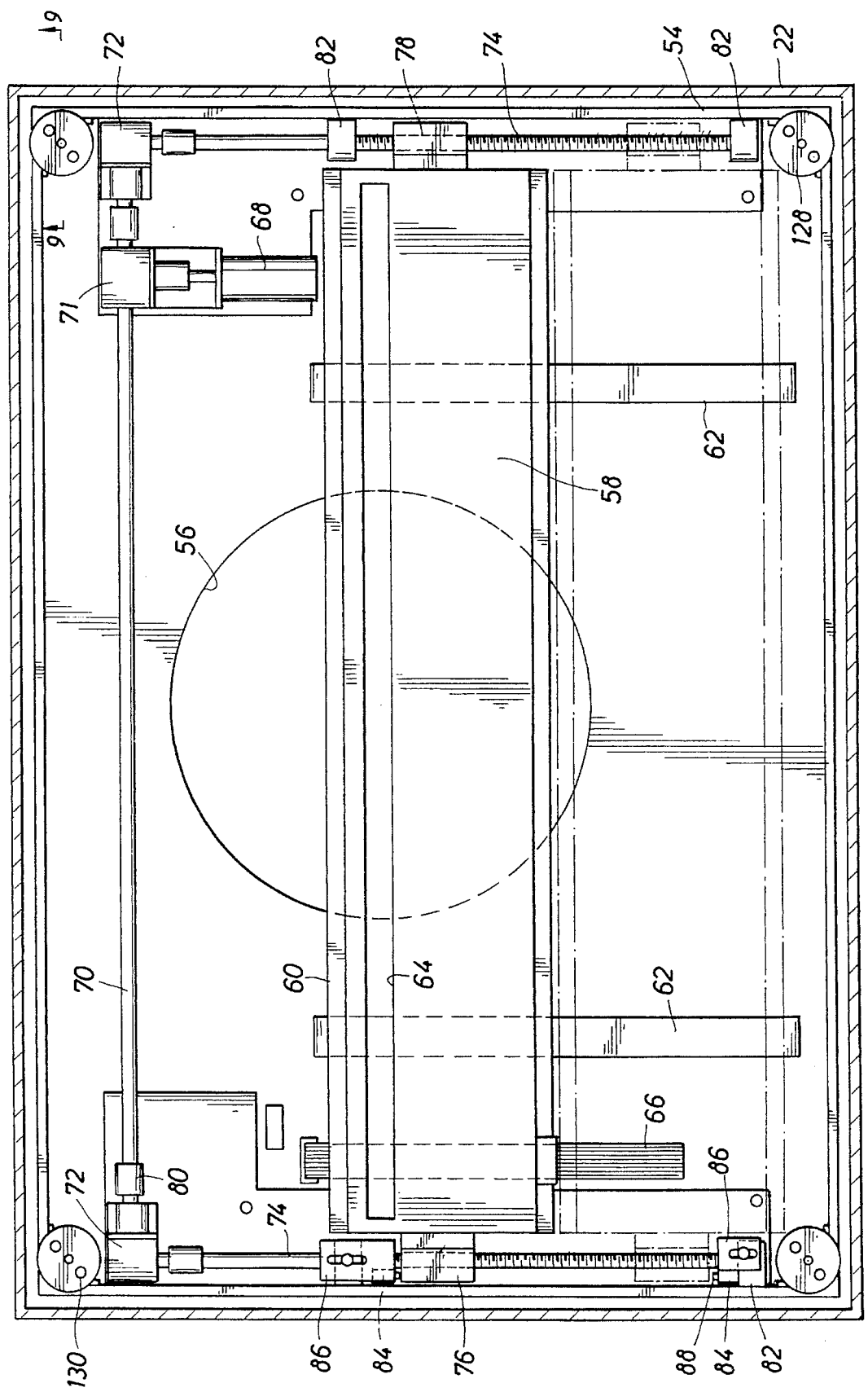

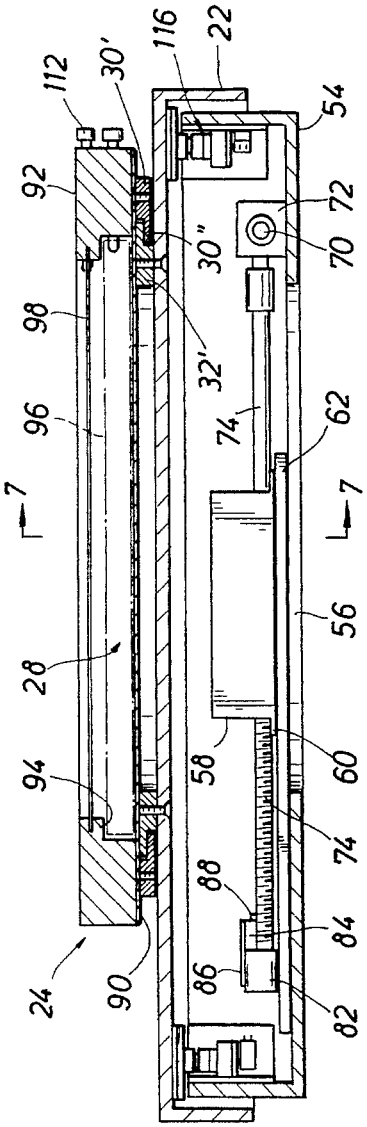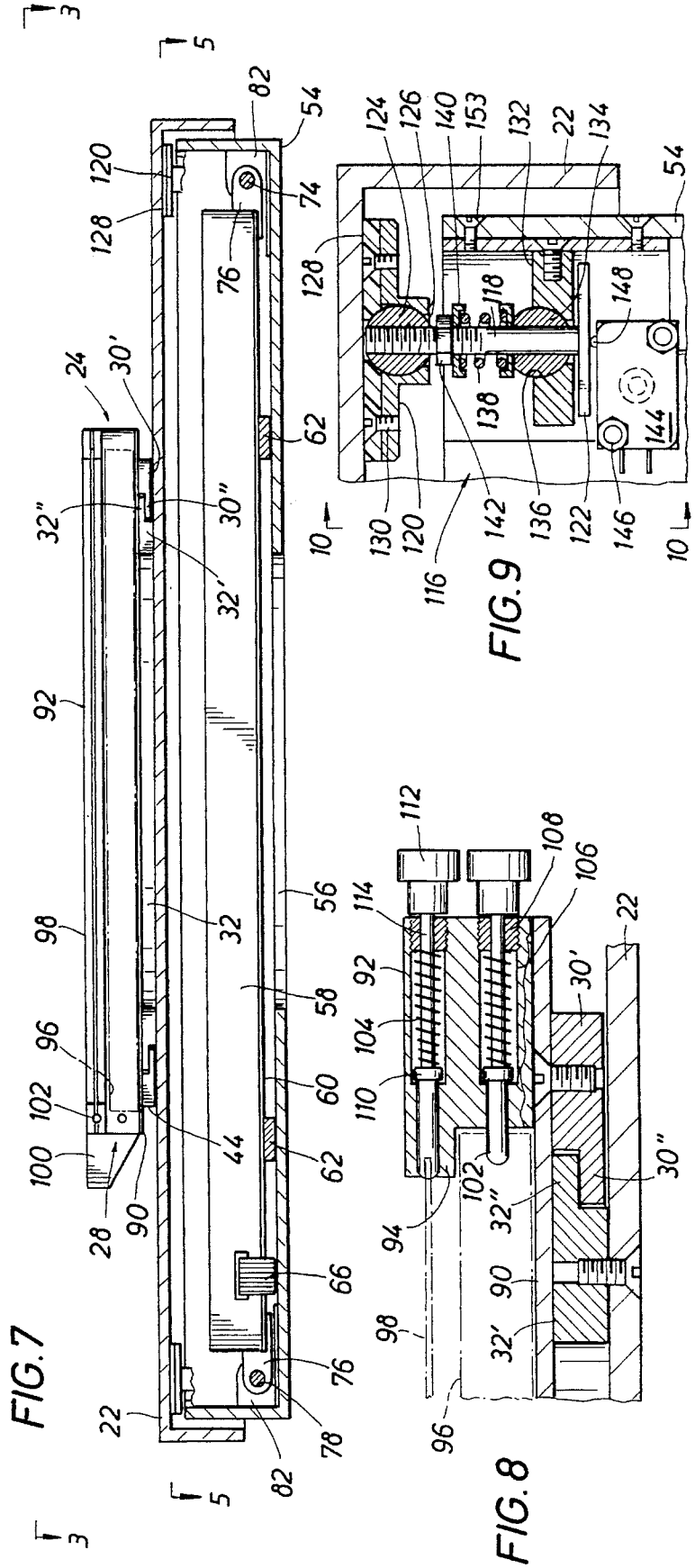

5,584,382

APPARATUS FOR DETECTING A CHANGE IN POSITION OF FIRST AND SECOND MEMBERS FOR USE IN MOUNTING THE DETECTOR ARRAY OF A CT SCANNER TO A RADIATION THEAPY SIMULATOR

This application is a continuation of application Ser. No. 08/194,848, filed on Feb. 14, 1994 and now abandoned, which application was a divisional of application Ser. No. 08/007,493, filed on Jan. 22, 1993, and now Pat. No. 5,317,617.

BACKGROUND OF THE INVENTION

The present invention relates to an apparatus for providing a safety override for use in connection with a detector array of a CT (computed tomography) scanner mounted to a conventional radiation therapy simulator (RTS) for use of the simulator to produce scans without inhibiting the simulator's fluoroscope and plain film acquisition modes when scans are not being acquired. More specifically, the apparatus of the present invention stops the rotation of the gantry or movement of the fixture supporting the image intensifier tube of the simulator in the event that an object is encountered during rotation or other movement, thereby decreasing the likelihood of damage to the apparatus of the present invention, the simulator, or the encountered object.

Other advantages, and the objects of the present invention will be apparent from the following detailed description of the preferred embodiment thereof.

SUMMARY OF THE INVENTION

The present invention is an apparatus for producing an output signal to, for instance, stop the rotation of the gantry of a radiation therapy simulator during a CT scan which is actuated by a stress on a first or second elongate member which tends to cause a change in the relative positions of the first and second members. The apparatus comprises a cap bearing against the first elongate member and having an elongate axis oriented in the same direction as the long axis of the first elongate member, a foot, and an elongate rod having the cap mounted to one end thereof and the foot mounted to the other end. A block is mounted at a fixed position relative to the second member and the rod passes through the block. A spring or other biasing means biases the cap away from the block, movement of the cap away from the block being limited by engagement of the block by the foot. A switch is positioned at a fixed position relative to the second member and on the other side of the foot from the block whereby movement of the first member relative to the second member resulting from a stress on the first member causes the foot to move against the bias of the spring to bear against the contact of the switch to produce an output signal indicative of the change in relative positions.

BRIEF DESCRIPTION OF THE DRAWINGS

FIG. 5 is a sectional view, taken along the lines 5—5 in FIG. 7, of the apparatus of FIG. 3.

FIG. 6 is a cross-sectional view taken along the lines 6—6 in FIG. 3.

FIG. 7 is a longitudinal sectional view taken along the lines 7—7 in FIG. 6.

FIG. 8 is a cross-sectional view of the apparatus of FIG. 3 similar to FIG. 6 but enlarged to show the details of the structure of a portion thereof.

FIG. 9 is a longitudinal sectional view similar to FIG. 7 but taken along the lines 9—9 in FIG. 5 and enlarged to show the details of the construction thereof.

DETAILED DESCRIPTION OF THE PREFERRED EMBODIMENT

Figure 1:
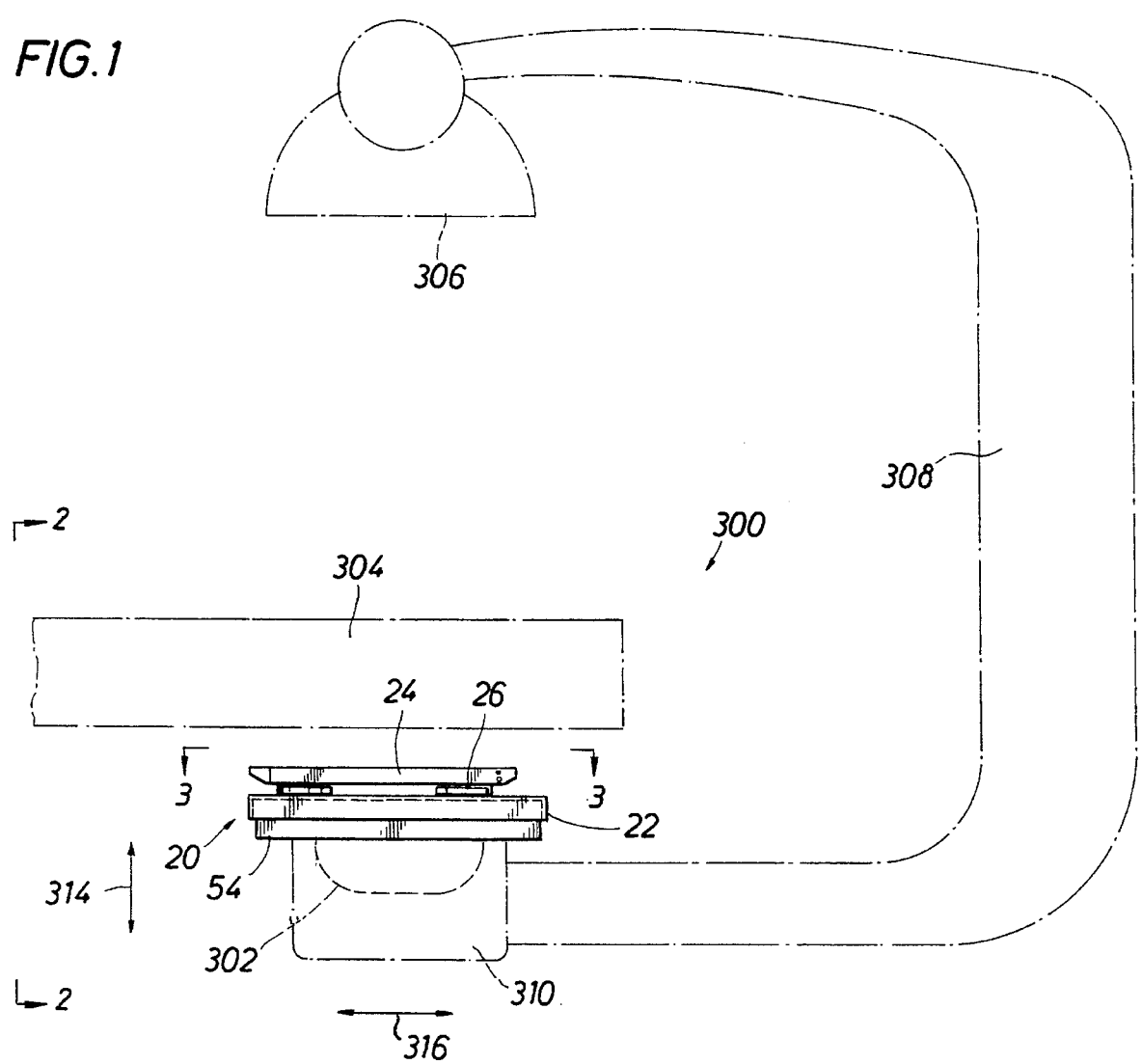
FIG. 1 is a diagrammatic, side view of a portion of a conventional radiation therapy simulator (shown in shadow lines) having the apparatus of the present invention mounted thereto.
Figure 2:
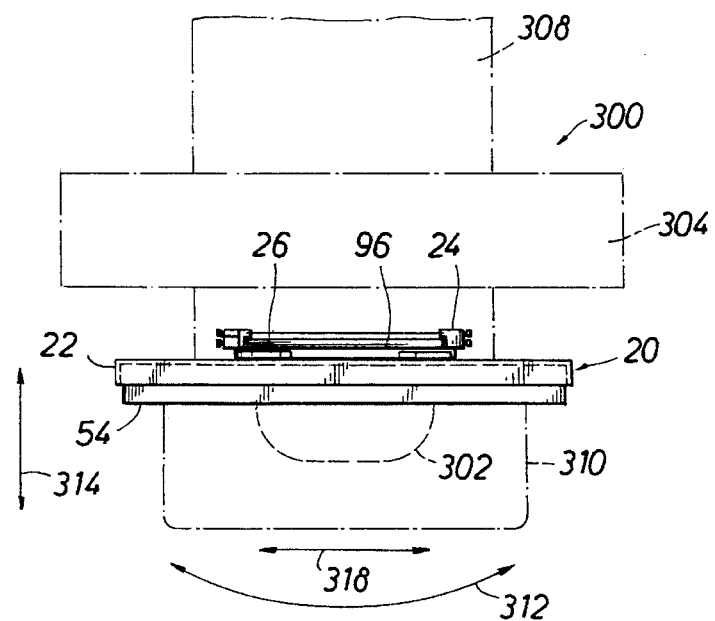
FIG. 2 is a front, partially cut-away view of the simulator of FIG. 1 taken from the lines 2—2 in FIG. 1.

Referring now to the figures, end and side views of the apparatus of the present invention, indicated generally at reference numeral 20, mounted over the image intensifier tube 302 of a radiation therapy simulator (RTS), shown in shadow lines at reference numeral 300, and below the x-ray table 304 of RTS, are shown in FIGS. 1 and 2, respectively. RTS 300 is any conventional simulator such as is known in the art and in common usage such as those manufactured by Odelft, Philips, Siemens, and Cascade X-Ray; particular success has been enjoyed in mounting the apparatus 20 to the Odelft and Philips simulators because of the interaction of the control circuitry of the apparatus 20 and the control circuitry of the RTS as described below. Portions of a generalized RTS 300 are shown in FIGS. 1 and 2, including, in addition to the image intensifier tube 302 and x-ray table 304, a radiation source 306, gantry 308, and fixture 310, the fixture 310 being integral with gantry 308 and supporting and housing the image intensifier tube 302 and, in the embodiment shown, the apparatus 20. It will be recognized by those skilled in the art that both radiation source 306 and image intensifier tube 302, having the apparatus 20 mounted thereto, rotate around the x-ray table 304 as much as 360°, e.g., in the direction of the arrows 312 in FIG. 2 (in and out of the plane of the paper with reference to FIG. 1). Fixture 310, as well as the portions of RTS 300 mounted and/or housed therein, also moves up and down (arrow 314), in and out (arrow 316), and side to side (arrow 318) under operator control with motors and controls which are not considered to constitute part of the present invention and therefore are not shown.

Figure 3:
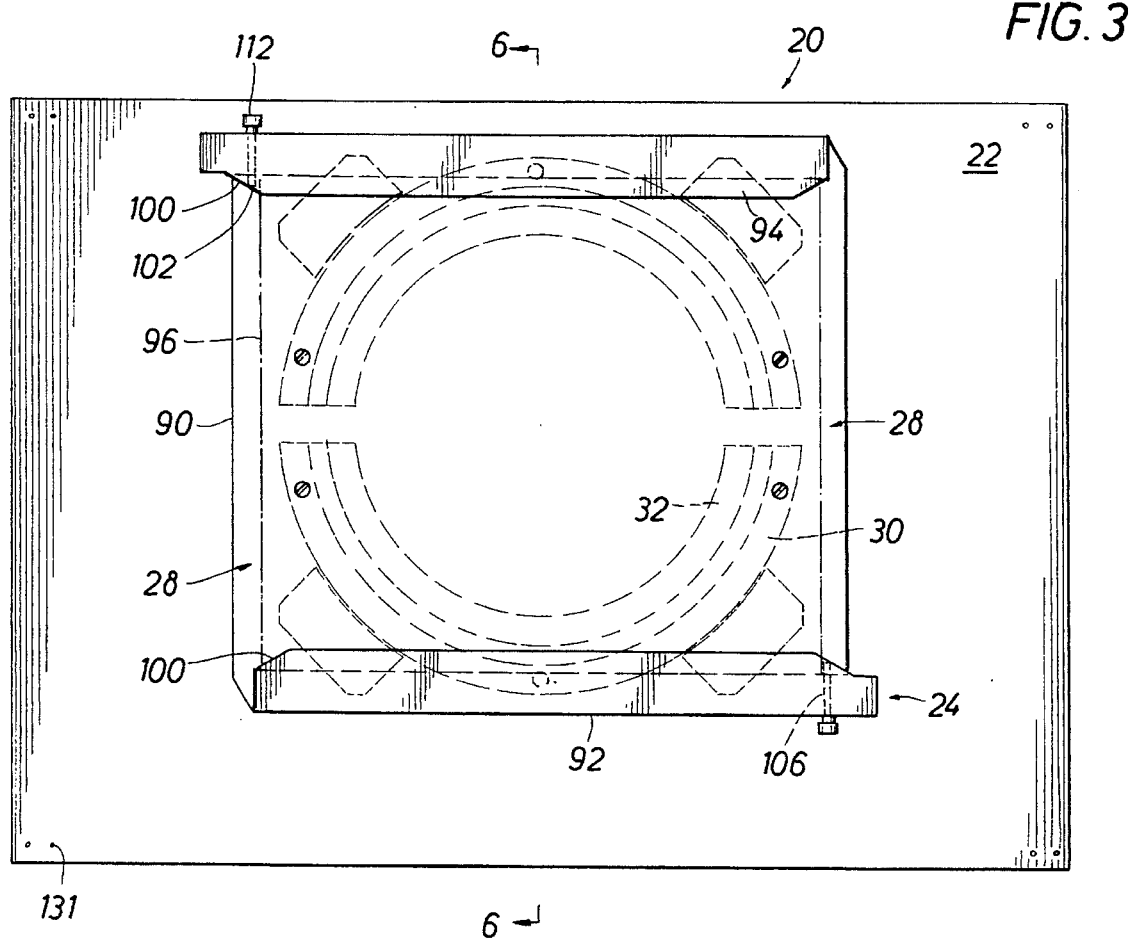
FIG. 3 is a top view of a preferred embodiment of the present invention taken from the position designated by the lines 3—3 in FIG. 1.
Figure 4:
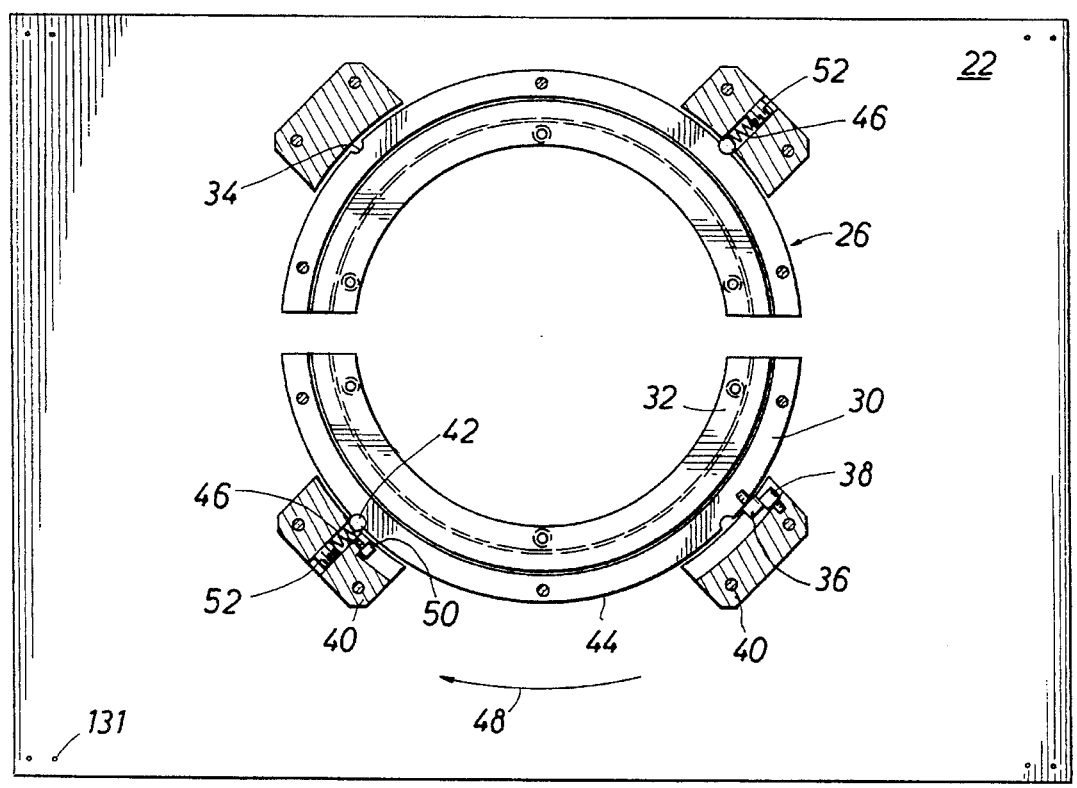
FIG. 4 is a view of the apparatus of FIG. 3 having had the film cassette holder removed therefrom.

Referring now to FIGS. 3 and 4, which are both top views of the apparatus 20 from below the x-ray table 304 shown in FIGS. 1 and 2 (see the arrows 3—3 in FIG. 1), the apparatus 20 is shown in more detail. Specifically, there is shown a radiolucent cover 22 to which a film cassette 24 is mounted on a set of concentric rings, or turntable, 26, the cassette holder 24 having been removed from the turntable 26 to show the details thereof in FIG. 4. Film cassette holder 24 is configured so as to slidably receive and retain an x-ray film cartridge and an x-ray grid for use of the RTS as a simulator and is shown in more detail in FIGS. 6, 7, and 8 and described infra in connection with the description of those figures. As is apparent from a comparison of FIGS. 1 and 2, film cassette holder 24 is mounted on turntable 26 to facilitate insertion of a film cassette into the holder 24 and to provide for acquisition of x-ray images with the long axis of the film either parallel or perpendicular to the long axis of table 304; the long axis of the x-ray table 304 runs right and left in FIG. 1 and in and out of the plane of the paper in FIG. 2 such that access to one open side 28 of film cassette holder 24 is limited by the length of x-ray table 304 when in the position shown in FIGS. 1 and 2 and by the gantry 308 on the other open side 28. Consequently, cassette holder 24 is rotated approximately 90° to the position shown in FIG. 3 either for exposure and/or so that loading and unloading of the film can be accomplished from the side of x-ray table 304, i.e., in and out of the plane of the paper in FIG. 1 and from the right or left of FIG. 2.

Turntable 26 is constructed of two concentric rings as follows. The outer concentric ring 30 is affixed to the film cassette holder 24, and is formed of two portions of different thicknesses (best illustrated in FIGS. 6–8), an outer portion 30' is thicker and is the portion through which the connection to film cassette holder 24 is made. The inner portion 30" is of lesser dimension and is received under the outer portion 32" of lesser dimension of the inner ring 32, the thicker, inner portion 32' being affixed to the cover 22 of apparatus 20. In a presently preferred embodiment, one or both of outer ring 30 and inner ring 32 are comprised of a material such as DELRIN® or aluminum, the former being preferred for its almost "self-lubricating" character. As can be seen in FIGS. 3 and 4, the concentric rings 30 and 32 comprising turntable 26 are preferably split; in other words, they do not form all 360° of the circumference of the circle. Being made of radio-opaque materials, the rings 30 and 32 are split to provide an opening through the turntable 26 through which the width-collimated fan beam produced by the radiation source 306 passes without being attenuated.

As also shown in FIGS. 3 and 4, turntable 26 is provided with means for limiting rotation of film cassette 24 and insuring the holding of the proper alignment of the film cartridge contained therein for acquisition of images with the long axis of cartridge 96 either parallel or perpendicular to the long axis of the table 304 and throughout the range of movement of fixture 310 and/or rotation of gantry 308. In the presently preferred embodiment shown in these figures, this rotation limiting and alignment means takes the form of the detents 34 formed in outer ring 30 and the stop 36 which is integrally mounted to that ring. The detents 34 and stop 36 function as follows. When the cassette holder 24 is in the position shown in FIG. 3 (and also in FIGS. 6 and 7), i.e., in the position in which access to the open sides 28 is not limited by x-ray table 304 for loading and unloading a film cassette 96, the stop 36 has been positioned so as to engage a similar stop 38 mounted in a block 40 which is integral with cover 22, e.g., in the position shown in FIG. 4. As is also apparent from FIG. 4, the balls 42 which are biased against the outside surface 44 of outer ring 30 by the springs 46 that are contained in similar blocks 40 engage the detents 34 formed in the outer surface of outer ring 30. Upon rotation of film cassette holder 24 by 90° in the direction of arrow 48 on FIG. 4, e.g., to the position shown in FIG. 1 in which access to the open sides 28 is obstructed by x-ray table 304, the stop 50 is engaged by stop 36 and the balls 42 engage the detents 34 located at 90° around the circle formed by ring 30 to limit rotation of the film holder 24 and hold the holder 24 in that position during gantry rotation or positioning of fixture 310. Precise alignment of film holder 24 in that position is obtained by backing the stop 50 in and out of block 40 on the threads formed in each of the block and stop. The amount of bias applied to the balls 42 is adjusted by use of an Allen wrench (not shown) in a slot formed in the threaded keepers 52 which engage the threads formed in blocks 40.

By reference to FIGS. 1–2 and 5–7, it can be seen that the cover 22 closes a tray 54 to form a substantially rectangular, closed box with a height dimension substantially less than the width and depth dimensions for fitting to simulator 300 over the image intensifier tube 302 and under x-ray table 304. An open circle 56 is cut in tray 54, e.g., in the bottom of the box, which fits over the image intensifier tube 302 of RTS 300, and is sized so as to fit over the housing of the tube 302 for attachment to RTS 300 by screws (not shown) or an adapter ring (not shown) which attaches to the housing by screws (housings are generally standardized in their outside diameter to either 9, 10, 12, or 14 inches in diameter, and in the preferred embodiment, opening 56 is 12 inches in diameter).

Mounted to tray 54 is a means for selectively moving the detector array 58 of an apparatus for acquiring computed tomographic (CT) scans from a first position outside of the field of radiation produced by the radiation source 306 of RTS 300 for use of RTS 300 for treatment planning purposes, e.g., for plain film and fluoroscopic acquisition modes, to a second position in the tray within the field of radiation produced by source 306 for use of RTS 300 as a CT scanner. Positioning means, in the preferred embodiment shown in the figures, takes the form of a caddy 60 which is slidable along the nylon ribs, or tracks, 62 mounted to the bottom of tray 54 for slidably supporting the caddy 60 and which is adapted for mounting the detector array 58 thereto. Although referred to herein as the detector array 58, those skilled in the art will recognize from this disclosure that the detector array is actually indicated generally at reference numeral 58, the detector elements themselves being contained within an outer cover with a slit 64 formed therein through which the width-collimated fan beam produced by the radiation source 306 passes so as to impinge upon the detector elements. Such detector arrays are available from, for instance, Thomson Electron Tubes Division, CSF Thomson et Cie (Paris, France), and output readings that are proportional to the degree of attenuation of the field by a target object positioned on the x-ray table 304 are sent to the signal processing components of the CTS (not shown) through a ribbon connector 66 which flexes as the detector array 58 slides from first to second position. Apparatus and a method for back projecting this attenuation data to compute CT scans is described in more detail in the above-described U.S. Pat. No. 5,293,312 and 5,307,264, both of which are hereby incorporated into the present application by this specific reference thereto. The detector array 58 is shown in the first position in shadow lines in FIG. 5 and is shown in the second position in FIGS. 5–7, and by comparison of FIGS. 3–4 to FIG. 5, it can be seen that when the detector array 58 is in the second position, the slit 64 therein is aligned with the above-described opening in the rings 30 and 32 comprising turntable 26 for passage of the x-ray beam therethrough.

In the preferred embodiment shown in the figures, the detector positioning means also comprises an electrically-controlled drive means for selectively sliding the caddy 60, having the detector array 58 mounted thereto, from the first to the second positions. This drive means preferably takes the form of an electric motor 68 mounted to tray 54 for turning, through transmission 71, the drive shaft 70, which rotation is translated through the right angle drives 72 to turn the screw shafts 74. The caddy 60 is provided with integral traveling blocks 76 at each end, so named because of the threaded bore 78 through each block which causes the caddy to slide along the rails 62 as the screw shafts 74 turn under the influence of motor 68. Flex couplings 80 are provided at intervals along the drive and shafts 70 and 74 as needed to minimize wear on the transmission 71, right angle drives 72, and traveling blocks 76, and the ends of shafts 74 are journaled in the bearings 82. The distance the caddy 60 travels from first position to second position or back to the first position is limited by the limit switches 84 integral with the plates 86 that are slidably mounted to bearing 82. When the activator 88 of one of the limit Switches 84 is contacted by the leading surface of traveling block 76, the switch causes motor 68 to turn off.

The details of the construction of film cassette holder 24 are also apparent from FIGS. 3 and 7–8. Cassette holder 24 is comprised of a radiolucent plate 90 to which side rails 92 are mounted. The inside edge of side rails 92 is provided with an overhanging portion 94 which, along with the lower portion of the inside edge of side rail 92 and the top surface of plate 90, serves to retain a film cassette, shown in shadow lines at reference numeral 96, in place in holder 24. A slot (not numbered) is formed in the overhang 94 of side rail 92 for receiving a grid 98 for preventing scatter of the x-ray beam as is known in the art. As best shown in FIG. 3, the side rails 92 and plate 90 are longer than the dimension of the standard size film cassette 96 so as to facilitate insertion of the film cassette 96 and grid 98 into their respective locations in cassette holder 24 from the open ends 28 thereof. Specifically, the plate 90 forms an edge on which the cassette 96 is rested and the inside corners of side rails 92 are beveled as at 100 so that the cassette 96 or grid 98 is more easily squared up and slid into holder 24. The side rails 92 are also provided with means for retaining the cassette 96 and grid 98 in place in their respective locations in holder 24 as the image intensifier tube 302, having the apparatus 20 mounted thereto, is rotated around the x-ray table 304 in the form of the spring-loaded pins 102 which protrude through the inside edges of side rails 92 at the open ends of holder 24. As best shown in FIG. 8, each of the pins 102 is biased in that direction by the spring 104 confined in the bore 106 in the side rail 92 by the threaded insert 108, the shoulder formed by the enlarged portion 110 of the pin 102 bearing against the shoulder formed by the change in internal diameter of bore 106. The knob 112 formed integrally with the shaft 114 of pin 102 facilitates the drawing of the pin 102 back into the bore 106 for insertion or withdrawal of the cassette 96 or grid 98.

The apparatus 20 of the present invention additionally comprises means for detecting a change in the height dimension of the closed box formed by the tray 54 and cover 22 or a change in dimension of a portion of the box (i.e., if one corner of the box encounters an object) such that the flat surfaces of tray 54 and cover 22 are not positioned in substantially paralled planes. In a particularly preferred embodiment, circuitry is also provided for stopping operation of the RTS 300 when the change detecting means is activated, e.g., for stopping gantry rotation or movement of the fixture 310 of the RTS 30Q. The height dimension of the box, or in a portion of the box, formed by tray 54 and cover 22 can be changed by, for instance, an encounter between the box and an object during rotation of the radiation source 306 and image intensifier tube 302, having the apparatus 20 mounted thereto or by the raising of the fixture 310 until the film cassette holder 24 encounters the underside of the table 310. Not only does the cessation of data collection from array 54, and the stopping of gantry rotation, prevent inaccurate readings from the array 58 resulting from the change in the distance from radiation source 306 to the detector array 58, but so also is damage to the apparatus 20, the CTS 300, or the encountered object avoided.

Figure 10:
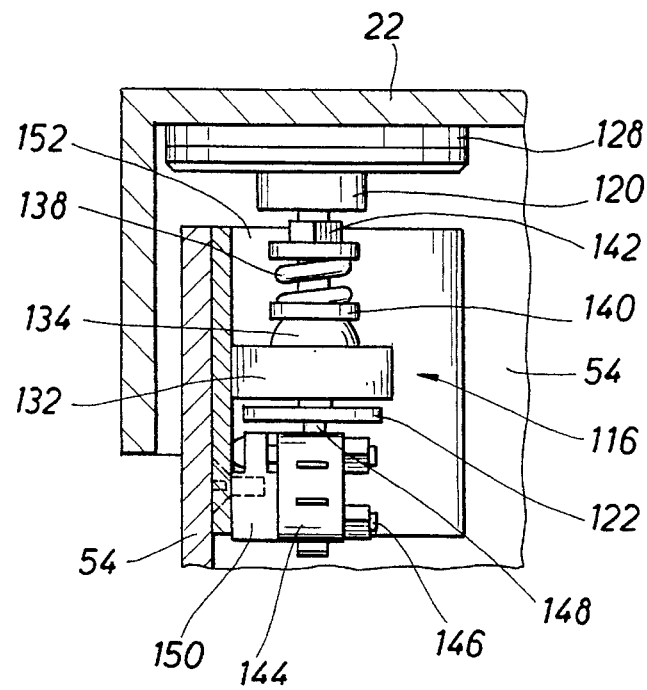
FIG. 10 is a cross-sectional view taken along the lines 10—10 in FIG. 9.
Figure 11:
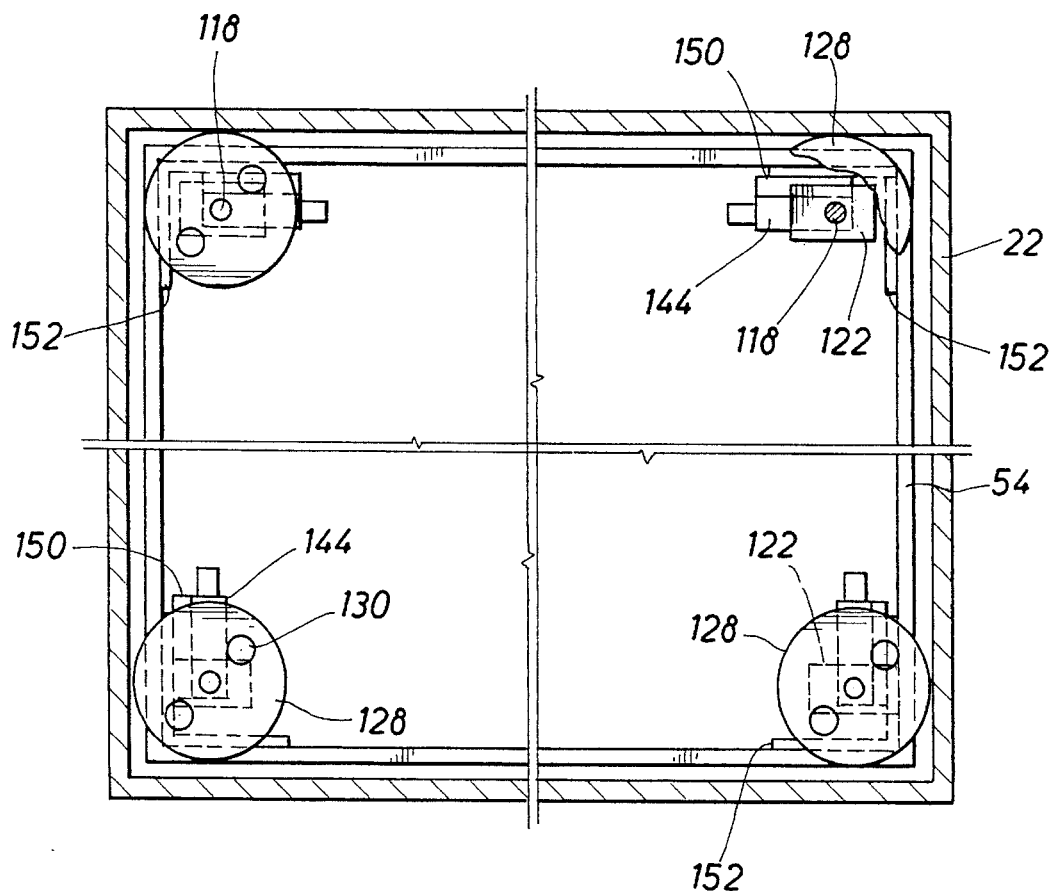
FIG. 11 is a partially cut-away sectional view similar to the view in FIG. 5 but with most of the internal structure of the apparatus omitted therefrom so as to show the details of the positioning and orientation of the defeats which is shown in FIG. 5.

As shown best in FIGS. 9–11, the drive means activator preferably takes the form of an apparatus for producing an output signal in the event of a change in the relative positions of cover 22 and tray 54 which is conveniently referred to as a defeat switch, and is indicated generally at reference numeral 116. Defeat switch 116 is comprised of an elongate rod 118 having a cap 120 mounted to one end thereof and a foot 122 integrally mounted to the other end, the cap 120 comprising a surface against which the under side of cover 22 bears. Cap 120 is preferably mounted to rod 118 through a ball and socket joint to allow relative motion between cap 120 and rod 118 in all possible directions, the joint being comprised of a ball 124 which is threadably received on rod 118 and which is confined within the socket 126 formed in cap 120. A bearing surface 128 is removably mounted to the cap 120 to close the socket 126 by screws 130. Note that cover 22 is secured to the bearing surface 128 by screws 131 (see FIGS. 3–4) and the relationship between the cover 22 and cap 120 is described in terms of the cover 22 "bearing" against cap 120 because the apparatus may be rotated through a 360° arc during either film image acquisition and/or CT scanning. Consequently, the cover 22 may actually be located under tray 54 at some point during the intended use of apparatus 20 and therefore must be secured to tray 54 to prevent the cover from falling off of tray 54.

The elongate rod 118 passes through a bore (not numbered) in a block 132 which is affixed to tray 54, and is preferably received through that bore in a second partial ball and socket type joint formed by the mounting of a ball 134 in the well 136 that is formed in block 132 and is contiguous with the bore through the block 132. Means, in the form of the spring 138 captured between the two cup washers 140 on rod 118, is provided for biasing cap 120 away from block 132, the tendency of cap 120 to move away from block 132 being limited by engagement of the underside of block 132 by the top surface of foot 122. A nut 142 is threaded onto the threads of rod 118 below ball 124 for adjusting the amount of bias between cap 120 and block 132. A switch 144 is positioned at a fixed position relative to tray 54 by the screws 146 on the other side of foot 122 from block 132 whereby movement of cap 126 towards block 132, e.g., against the bias applied by spring 138, causes the underside of foot 122 to bear against the actuator 148 of switch 144 to produce an output signal indicating a change in the relative positions of cover 22 and tray 54.

For convenience and interchangeability, switch 144 is mounted to a shim 150 (best shown in Fig. 10) by screws 146, the shim 150 being mounted to L-bracket 152, and L-bracket 152 is affixed to tray 54 by screws 153 so that the entire defeat switch 116 is conveniently removed from tray 54. Mounting of the defeat switch 116 on L-bracket 152 facilitates the mounting of a switch 116 at each of the four corners of the box formed by tray 54 and cover 22, with cover 22 being secured to the bearing surfaces 128 of each cap 120, as best shown in FIGS. 5 and 11.

By reference to FIG. 11, it can also be seen that the foot 122 of each switch 116 is rectangularly-shaped and that the long axis of the foot 122 is oriented in substantially the same direction as the long axis of the rectangularly-shaped box. By elongating the foot 122 in the direction of the long axis of the box, the actuator 148 of switch 144 is contacted even in the event of the relatively small change in the relative positions of tray 54 and cover 22, which results from, or is indicative of, a relatively large change in the relative positions of tray 54 and cover 22 at a point remote from the point at which cover 22 bears against cap 120. Another benefit of this elongation of foot 122 is that the bias applied to each defeat switch 116 by spring 138 need not be adjusted to compensate for the unsprung weight of the components of apparatus 20 throughout the range of movement of the defeat switch 116 as the gantry 308 of RTS 300 rotates around table 304 and the switch is activated by the same amount of force resulting from an object bearing against cover 22 regardless of whether cover 22 encounters an object along the long or the short axis of the box. In other words, although the force vectors having components in a direction opposing the bias applied to the cap 120 of defeat switch 116 by spring 138 changes during gantry rotation, no compensation for that change need be made to prevent actuator between foot 122 and the contact 148 of switch 144 because the shape of foot 122 effectively compensates for the different forces applied to the defeat switch 116 along different vectors by the changing weight of cover 22 or by an encountered object during rotation (or during movement of the fixture 310 as described above).

Although described in terms of the preferred embodiment shown in the figures, the present invention is not so limited. Those skilled in the art who have the benefit of this disclosure will recognize that many changes can be made to the component parts described herein without changing the manner in which these parts function to achieve their intended result. For instance, the cap 120 of defeat switch 116 can be biased away from block 132 by a magnetic (or electromagnetic) field rather than with the spring 138. The electrically-controlled drive means described herein for positioning the detector array 58 in first and second positions can be belt driven (instead of using the shafts 70 and 74 and bearings 82) or a pneumatic cylinder under control of a switch can be utilized rather than the motor 68. Further, it will be apparent that the ability of defeat switch 116 to signal a change in the relative positions of tray 54 and cover 22 is not limited to the specific application described herein and that defeat switch 116 can be used for that purpose in connection with any first and second member, and is especially useful when one or both of the first and second members is elongated in a direction in which the long axis of the foot 132 can be oriented or when one or the other of the members is exposed to different degrees of stress in a direction along which the long axis of the foot can be oriented. All such changes are intended to fall within the spirit and scope of the following claims.

What is claimed:

1. An apparatus for producing an output signal in the event of a change in the positions of a first elongate member and a second member relative to each other comprising:
   a cap bearing against the first elongate member;
   a rectangularly-shaped foot having the long axis thereof oriented in the same direction as the long axis of the first elongate member;
   an elongate rod having said cap mounted to one end thereof and said foot mounted to the other end;
   a block having a socket formed therein mounted at a fixed position relative to the second member and having said rod passing therethrough;
   a ball mounted in the socket in said block and having said rod passing through a bore therein;
   means biasing said cap away from said block; and
   a switch having an actuator positioned at a fixed position relative to the second member whereby movement of the first elongate member relative to the second member causes movement of said foot against the bias of said bias means causing said foot to bear against the actuator of said switch to produce an output signal indicating a change in the relative positions of the first elongate member and the second member.

2. The apparatus of claim 1 additionally comprising means for adjusting the bias applied by said bias means.

3. The apparatus of claim 1 wherein said first member comprises a cover and said second member comprises a tray of a box for mounting the detector array of a CT scanner to a radiation therapy simulator.

4. An apparatus for producing an output signal in the event of a change in the positions of a cover and tray of a box for mounting the detector array of a CT scanner to a radiation therapy simulator, the cover and tray being rectangularly-shaped so as to have a long axis and a short axis, relative to each other comprising:
   a cap bearing against the cover;
   a rectangularly-shaped foot the long axis of which is oriented in the same direction as the long axis of the cover;
   an elongate rod having said cap mounted to one end thereof and said foot mounted to the other end;
   a block mounted at a fixed position relative to the the tray and having said rod passing therethrough;
   means biasing said cap away from said block; and
   a switch having an actuator positioned at a fixed position relative to the tray whereby movement of the cover relative to the tray causes movement of said foot against the bias of said bias means causing said foot to bear against the actuator of said switch to produce an output signal indicating a change in the relative positions of the cover and tray.

* * * * *